(12) United States Patent
Burdeniuc

(10) Patent No.: US 6,548,670 B1
(45) Date of Patent: Apr. 15, 2003

(54) METHODS FOR PREPARING 5- AND 6-BENZYL-FUNCTIONALIZED QUINOXALINES

(75) Inventor: Juan Jesus Burdeniuc, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/909,002

(22) Filed: Jul. 19, 2001

(51) Int. Cl.$^7$ .............................................. C07D 241/42
(52) U.S. Cl. ...................................................... 544/353
(58) Field of Search ........................................ 544/353

(56) References Cited

U.S. PATENT DOCUMENTS

| | | |
|---|---|---|
| 3,960,963 A | 6/1976 | Gavin |
| 5,028,606 A | 7/1991 | Venet et al. |
| 6,492,517 B1 * | 12/2002 | Burdeniuc |

FOREIGN PATENT DOCUMENTS

| | | |
|---|---|---|
| EP | 0322255 | 6/1989 |
| EP | 0381375 | 8/1990 |
| EP | 0385662 | 9/1990 |
| EP | 0385663 | 9/1990 |
| JP | 02223558 | 9/1990 |
| WO | WO9843959 | 10/1998 |

OTHER PUBLICATIONS

European Search Report, 02015578.4–1521, dated Nov. 19, 2002.
K. C. Murdock, et al., "Antitubercular 2, 8–bis(alkylaminomethyl) phenazines," J. Med. Chem., vol. 21, No. 4 (1978), pp. 403–405. (Abstract).
M. L. Edwards, et al., "Formyl–substituted phenazine 5, 10–dioxides," J. Hetercycl. Chem., vol. 13, No. 3 (1976), pp. 653–656. (Abstract).
M. Uchida, et al., "Studies on proton pump inhibitors. II. Synthesis and antiulcer activity of 8–'(2–benzimidazolyl) sulfinylmethyl'—1, 2, 3, 4—tetrahydroquinolines and related compounds," Chem. Pharm. Bull., vol. 37, No. 8 (1989), pp. 2109–2116. (Abstract).
K. P. Butin, et al., " Solvolytic cleavage of 1–(8–qunolyl) ethyl mercury bromide I methanol," Izv. Akad. Nauk SSSR, Ser. Khim., No. 2 (1985), pp. 443–447. (Abstract).
A. Sugimoto, et al., "Synthesis and inhibitory effect on platelet aggregation of 2–phenyl–1(2H)–phthalazinone derivatives," Chem. Pharm. Bull., vol. 33, No. 7 (1985), pp. 2809–2820. (Abstact).
P. R. Marsham, et al., " Quinazoline antifolate thymidylate synthase inhibitors: Heterocyclic benzoyl ring modifications," Journal of Medicinal Chemistry, vol. 34, No. 5 (1991), pp. 1594–1605. (Abstract).
A. Niimi, et al., " Synthesis of alkylaminomethylisoquinoline and N–alkylbeno 'de' 1, 7 naphthyridinim bromide from bromomethylisoquinolines and amines," Chemistry Express, vol. 6, No. 1 (1991), pp. 45–48. (Abstract).
C. Ruddick, et al., "Conversion of alkyl halides into the corresponding alcohols under mld reaction conditions," Synthesis, No. 11 (1996), pp. 1359–1362. (Abstract).
N. Maigrot, et al., "New and improved synthesis of optically pure (R)– and (S)–2,2 '–dimethyl–1, 1'–binaphthyl and related compounds," Synthesis, No. 3 (1985), pp. 317–320. (Abstract).
K. H. Duchene, et al., "New helical molecules. 12. The first '2.1 phane. A new helical molecular skeleton," Angew. Chem., vol. 97, No. 10 (1985), p. 866. (Abstract).
D. N. Dhydyrov, et al., "Some reactions based on the sulfhydryl group of 1–naphthylmethanethiol," Azerb. Khim. Sh., No. 2 (1978), pp. 53–56. (Abstract).
F. Ebmeyer, et al., "Template synthesis of macrobicyclic large cavities of the tris (bipyridine) type," Chem. Ber., vol. 122, No. 9 (1989), pp. 1725–1727. (Abstract).
D. Michelot, et al., "Preparation of aldehydes by sigmatropic 2, 3 rearrangement of beta gamma.—unsaturated ammonium ylides bearing thio ether groups on the anionic carbon atom," Bull. Soc. Chim. Fr. (1976), (9–10, PT.2), pp. 1482–1488. (Abstract).
G. W. H. Chesseman, in "Advances in Heterocyclic Chemistry" by A. R. Katrizky Academic Press, vol. 2, pp. 203–221, 1963.
J. C. Cavagnol, F. Y. Wiselogle, "1–Alkyl–1,2,3,4–Tetrahydroquinozalines", J. Am. Chem. Soc., 69, 795, 1947.
O. Gawron and P. Spoerri, "7–Methoxy–5–Aminoquinoxaline and 7–Methoxy–5–diethylamineoalkylamino–Quinoxalines", J. Am. Chem. Soc., 67, 514, 1945.
R. Mizzoni, P. E. Spoerri, J. Am. Chem. Society, 67, 1652, 1945.
O. Gawron, A. Rampal and P. Johnson, J. Am. Chem. Soc., 94, 5396, 1972.
R. C. DeSelms, R. J. Greaves, W. R. Schleigh, J. Heterocyclic Chem., 11, 595, 1974.
R. Granger, S. Deadwyler, M. Davis, et al. Synapse, 22, pp. 332–337, 1996.
G. Lynch, M. Kessler, et al., International Clinical Psycopharmacology, 11, pp. 13–19, 1996.
2,3–Pyrazinedicarboxylic Acid: "organic Synthesis" Coll. vol. 4 pp. 824–827, J. Wiley & Sons, Inc. NY, 1963.

* cited by examiner

*Primary Examiner*—Emily Bernhardt
(74) *Attorney, Agent, or Firm*—Michael Leach

(57) ABSTRACT

The present invention pertains to methods for preparing 5- and 6-benzyl functionalized quinoxalines. In a first embodiment, the method comprises contacting an aqueous suspension of a 5- and 6-halomethyl quinoxaline with a water-soluble nucleophile. In a second embodiment, the method comprises contacting a 5- and 6-halomethyl quinoxaline with an organic solvent-soluble nucleophile in an inert polar organic solvent. In a third embodiment, the method comprises contacting a 5- and 6-halomethyl quinoxaline in an organic solvent with an aqueous solution of a water-soluble nucleophile in the presence of a phase transfer catalyst.

10 Claims, No Drawings

METHODS FOR PREPARING 5- AND 6-BENZYL-FUNCTIONALIZED QUINOXALINES

BACKGROUND OF THE INVENTION

The present invention relates to a method for preparing 5- and 6-benzyl functionalized quinoxalines.

The disclosures referred to herein to illustrate the background of the invention and to provide additional detail with respect to its practice are incorporated herein by reference and, for convenience, are numerically referenced in the following text and respectively grouped in the appended bibliography.

Substituted quinoxalines are important chemical intermediates for the preparation of pharmaceutical compounds, such as AMPHAKINE CX516® [1-(quinoxalin-6-ylcarbonyl)piperidine]. Substituted quinoxalines are typically prepared by condensation of substituted ortho-diaminobenzenes with sodium glyoxal bisulfite as set out below (1).

For example, 7-methoxy-5-aminoquinoxaline has been prepared by condensation of 3,4,5-triaminoanisole with sodium glyoxal bisulfite (2).

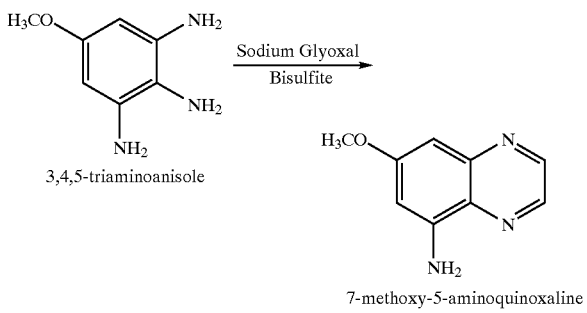

7-methoxy-5-aminoquinoxaline

Similarly, 7-methoxy-5-aminoquinoxaline and 7-methoxy-5-hydroxyaminoquinoxaline have been prepared from 3,5-dinitro-4-aminoanisole, which in turn was prepared by nitration of m-nitrobenzenesulfonyl-p-aminoanisole (3).

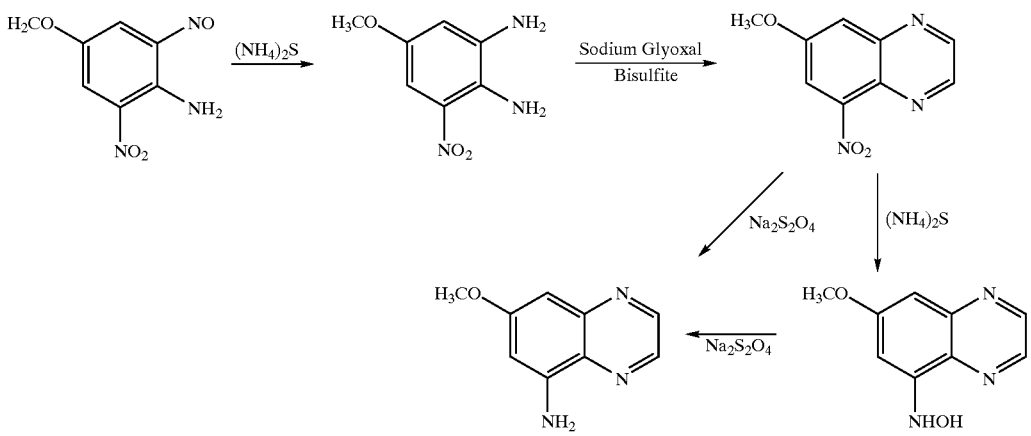

Nevertheless, there are no reported procedures for preparing 6-hydroxymethylquinoxaline by condensation of 3,4-diaminohydroxymethylbenzene with sodium glyoxal bisulfite, presumably because such a method is not trivial and requires multiple steps. Because attempts to prepare 5- and 6-benzyl functionalized quinoxalines via a one-step selective reaction of the benzyl group were not successful, a two-step method to prepare 5- and 6-benzyl functionalized quinoxalines was developed.

BRIEF SUMMARY OF THE INVENTION

In a first embodiment, the present invention pertains to a method for preparing a compound having Formula (I).

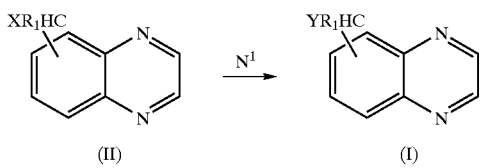

In this first embodiment, the method comprises contacting an aqueous suspension of a compound having Formula (II) with a water-soluble nucleophile, $N^1$, containing moiety Y; wherein X is chloro or bromo; $R_1$ is selected from the group consisting of hydrogen and branched and unbranched alkyl and aryl groups having from 1 to 9 carbon atoms; Y is selected from the group consisting of $-OR_2$, $-NHR_2$, $-NR_2R_3$, $-SR_2$, and $-CN$; and $R_2$ and $R_3$ are independently selected from the group consisting of hydrogen and branched and unbranched alkyl groups having from 1 to 4 carbon atoms.

In a second embodiment, the present invention pertains to a method for preparing a compound having Formula (I).

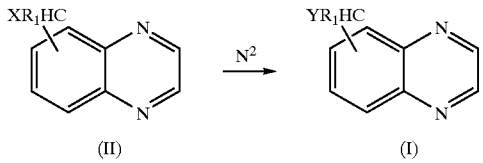

In this second embodiment, the method comprises contacting a compound having Formula (II) with an organic solvent-soluble nucleophile, $N^2$, containing moiety Y, in an inert polar organic solvent; wherein X is chloro or bromo; $R_1$ is selected from the group consisting of hydrogen and branched and unbranched alkyl and aryl groups having from 1 to 9 carbon atoms; Y is selected from the group consisting of —$OR_2$, —$NHR_2$, —$NR_2R_3$, and —$SR_2$; and $R_2$ and $R_3$ are independently selected from the group consisting of hydrogen and branched and unbranched alkyl and aryl groups having from 5 to 9 carbon atoms.

In a third embodiment, the present invention pertains to a method for preparing a compound having Formula (I).

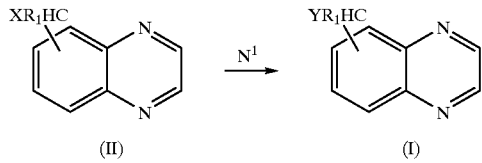

In this third embodiment, the method comprises contacting a compound having Formula (II) in an organic solvent with an aqueous solution of a water-soluble nucleophile, $N^1$, containing moiety Y, in the presence of a phase transfer catalyst; wherein X is chloro or bromo; $R_1$ is selected from the group consisting of hydrogen and branched and unbranched alkyl and aryl groups having from 1 to 9 carbon atoms; Y is selected from the group consisting of —$OR_2$, —$NHR_2$, —$NR_2R_3$, —$SR_2$, and —CN; and $R_2$ and $R_3$ are independently selected from the group consisting of hydrogen and branched and unbranched alkyl groups having from 1 to 4 carbon atoms.

DETAILED DESCRIPTION OF THE INVENTION

The present invention pertains to methods for preparing 5- and 6-benzyl functionalized quinoxalines. In a first embodiment, the method comprises contacting an aqueous suspension of a 5- and 6-halomethyl quinoxaline with a water-soluble nucleophile. In a second embodiment, the method comprises contacting a 5- and 6-halomethyl quinoxaline with an organic solvent-soluble nucleophile in an inert polar organic solvent. In a third embodiment, the method comprises contacting a 5- and 6-halomethyl quinoxaline in an organic solvent with an aqueous solution of a water-soluble nucleophile in the presence of a phase transfer catalyst.

The 5- and 6-halomethyl quinoxalines may be prepared from 5- and 6-methyl quinoxalines, which in turn may be prepared from ortho-diaminotoluenes, such as 2,3-and 3,4-diaminotoluene, by condensation with sodium glyoxal bisulfite. The preparation of ortho-diaminotoluenes is not trivial because the nitration of toluene yields mainly 2,4-dinitrotoluene, the precursor of 2,4-diaminotoluene (TDA, toluene-diamine), and only 4% or less of the ortho-isomers. However, 2,4-diaminotoluene is a bulk chemical, from which the ortho-diamine isomers are removed by distillation, and consequently uses for the ortho-diamine by-products are desired. The present invention provides a simple route to compounds such as 6-hydroxymethyl-quinoxaline by taking advantage of the availability of ortho-toluene diamine (OTD) using selective functionalization of the methyl group without affecting the aromatic rings.

Because attempts to prepare 5- and 6-benzyl functionalized quinoxalines via a one-step selective reaction of the benzyl group were not successful, a two-step method to prepare 5- and 6-benzyl functionalized quinoxalines was developed.

In the first step, a 5- or 6-benzyl-quinoxaline is halogenated to provide the corresponding 5- or 6-halomethyl-quinoxaline intermediate.

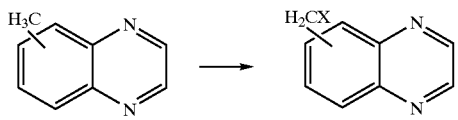

X is halogen. The term "halogen", as used herein, refers to fluorine, chlorine, bromine, and iodine. Preferred halogens are chlorine and bromine.

In the first step of the synthesis, a benzylic methyl heterocyclic compound and a halogenating agent, such as N-chlorosuccinimide (NCS) or N-bromosuccinimide (NBS), are reacted in the presence of a radical initiator, such as benzoyl peroxide or azobisisobutyronitrile, in a suitable solvent, to form the respective 5- or 6-halomethyl quinoxaline (I). Suitable solvents may be selected from the group consisting of fluorobenzene, difluorobenzenes, trifluorobenzenes, chlorobenzene, dichlorobenzenes, trichlorobenzenes, α,α,α-trifluorotoluene and α,α,α-trichlorotoluene. The method typically affords good yields of halomethyl-quinoxalines when [6QX]/[benzoyl peroxide] ≦40 while maintaining a temperature in the range of 60° C. to 115° C. for a period of 1 to 12 hours. Yields for benzylic brominations (conversions≧95%, selectivities≧97%) are in general better than for benzylic chlorinations (conversions 60%, selectivities~75–80%). The 5- or 6-halomethyl quinoxaline may be a 5-halomethyl quinoxaline or may be a 6-halomethyl quinoxaline. The halomethyl may be a chloromethyl or may be a bromomethyl.

This first step is more fully described in a patent application Ser. No. 09/909,000, now U.S. Pat. No. 6,492,517 entitled "Method For Preparing Halomethyl Heterocyclic Compounds" filed by Applicant concurrently on Jul. 19, 2001 with the present patent application, and assigned to the assignee of this application, which is hereby incorporated by reference.

In the second step, the 5- or 6-halomethyl-quinoxaline intermediate (II) is contacted with a nucleophile to yield the corresponding 5- or 6-benzyl functionalized quinoxaline (I).

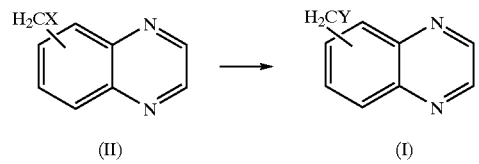

In a first embodiment, the present invention pertains to a method for preparing a compound having Formula (I) which comprises contacting an aqueous suspension of a compound having Formula (II) with a water-soluble nucleophile, $N^1$, containing moiety Y.

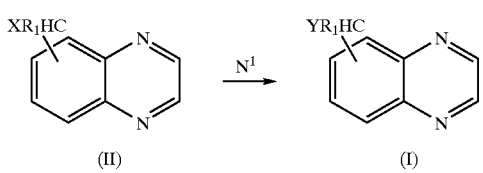

In this first embodiment, the compound having Formula (I) may be:

or may be

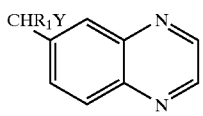

$R_1$ may be selected from the group consisting of hydrogen and branched and unbranched alkyl and aryl groups having from 1 to 9 carbon atoms. Preferably, $R_1$ is selected from the group consisting of hydrogen and branched and unbranched alkyl and aryl groups having from 1 to 6 carbon atoms, more preferably $R_1$ is selected from the group consisting of hydrogen and branched and unbranched alkyl groups having from 1 to 3 carbon atoms, and most preferably $R_1$ is hydrogen.

The water-soluble nucleophiles, $N^1$, containing moiety Y, which may be employed in the present invention may be any water-soluble nucleophile which is capable of selectively displacing the halogen group attached to the benzylic position of the heterocyclic compound in an aqueous suspension. The term "water-soluble nucleophile", as used herein, refers to a nucleophile that can be dissolved in water to yield a solution with a molarity equal to, or greater than, 0.01. Non-limiting illustrative water-soluble nucleophiles are those that contain a Y moiety, where Y may be selected from the group consisting of —$OR_2$, —$NHR_2$, —$NR_2R_3$, —$SR_2$, and —CN. $R_2$ and $R_3$ are independently selected from the group consisting of hydrogen and branched and unbranched alkyl groups having from 1 to 4 carbon atoms. Preferably, $R_2$ and $R_3$ are independently selected from the group consisting of hydrogen and branched and unbranched alkyl groups having from 1 to 3 carbon atoms, more preferably $R_2$ and $R_3$ are independently selected from the group consisting of hydrogen and alkyl groups having from 1 to 2 carbon atoms, and most preferably $R_2$ and $R_3$ are hydrogen. Preferred water-soluble nucleophiles may be selected from the group consisting of alkali hydroxides and alkaline earth hydroxides. More preferred water-soluble nucleophiles may be selected from the group consisting of lithium hydroxide, sodium hydroxide, and potassium hydroxide. Preferably, Y is hydroxy.

In a second embodiment, the invention is directed to a method for preparing a compound having Formula (I) which comprises contacting a compound having Formula (II) with an organic solvent-soluble nucleophile, $N^2$, containing moiety Y, in an inert polar organic solvent.

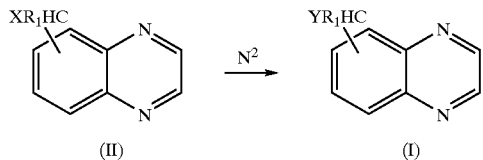

In this second embodiment, the compound having Formula (I) may be:

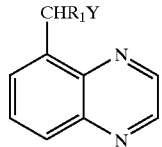

or may be

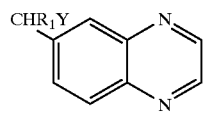

The definition of X and $R_1$ are as defined above.

The organic solvent-soluble nucleophiles which may be employed in the present invention may be any organic solvent-soluble nucleophile which is capable of selectively displacing the halogen group attached to the benzylic position of the heterocyclic compound in an inert polar organic solvent. The term "organic solvent-soluble nucleophile", as used herein, refers to a nucleophile that can be dissolved in an organic solvent to yield a solution with a molarity equal to, or greater than, 0.01. Non-limiting illustrative organic solvent-soluble nucleophiles are those that contain a Y moiety, where Y may be selected from the group consisting of —$OR_2$, —$NHR_2$, —$NR_2R_3$, and —$SR_2$. $R_2$ and $R_3$ are independently selected from the group consisting of hydrogen and branched and unbranched alkyl and aryl groups having from 5 to 9 carbon atoms. Preferably, $R_2$ and $R_3$ are independently selected from the group consisting of hydrogen and branched and unbranched alkyl and aryl groups having from 5 to 8 carbon atoms, more preferably $R_2$ and $R_3$ are independently selected from the group consisting of hydrogen and branched and unbranched alkyl and aryl groups having from 5 to 7 carbon atoms, and most preferably $R_2$ and $R_3$ are hydrogen. Preferred organic solvent-soluble nucleophiles may be selected from the group consisting of benzyltrimethyl ammonium hydroxide, tetrabutyl ammonium hydroxide, alkyl alcohols, aryl alcohols, alkylamines, arylamines, alkyl sulfides, aryl sulfides, and the salts thereof. More preferred organic solvent-soluble nucleophiles are benzyltrimethyl ammonium hydroxide and tetrabutyl ammonium hydroxide. Preferably, Y is hydroxy.

The inert polar organic solvents which may be employed in the present invention may be any inert polar organic solvent which is capable of dissolving the organic solvent-soluble nucleophile and the 5- or 6-halomethyl quinoxaline thereby permitting the selective displacement of the halogen group attached to the benzylic position of the heterocyclic compound. The term "inert polar organic solvent", as used herein, refers to an organic solvent that does not react with the organic solvent-soluble nucleophile or the 5- or 6-halomethyl quinoxaline and promotes a reaction between the organic solvent-soluble nucleophile and the 5- or 6-halomethyl quinoxaline. Non-limiting illustrative inert polar organic solvents may be selected from the group consisting of tetrahydrofuran, dioxane, 2-methoxyethyl ether, triethylene glycol dimethyl ether, dimethylsulfoxide (DMSO), methyl-tert-butyl ether (MTBE), and diethyl ether. Preferred inert polar organic solvents may be selected from the group consisting of tetrahydrofuran, dioxane, 2-methoxyethyl ether, triethylene glycol dimethyl ether, and dimethylsulfoxide. More preferred inert polar organic solvents may be selected from the group consisting of tetrahydrofuran, dioxane, and 2-methoxyethyl ether. Most preferred inert polar organic solvents are tetrahydrofuran and dioxane.

In a third embodiment, the invention is directed to a method for preparing a compound having Formula (I) which comprises contacting a compound having Formula (II) in an organic solvent with an aqueous solution of a water-soluble nucleophile, $N^1$, containing moiety Y, in the presence of a phase transfer catalyst.

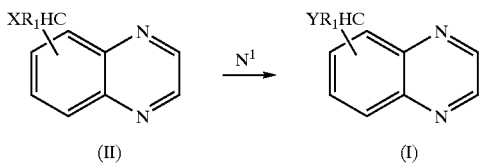

In this third embodiment, the compound having Formula (I) may be:

or may be

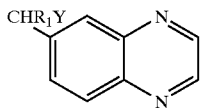

The definition of X, $R_1$, and the water-soluble nucleophile are as defined above.

The organic solvents which may be employed in the present invention may be any organic solvent which is capable of dissolving the water-soluble nucleophile and the 5- or 6-halomethyl quinoxaline with the assistance of the phase transfer catalyst thereby permitting the selective displacement of the halogen group attached to the benzylic position of the heterocyclic compound. Non-limiting illustrative organic solvents may be selected from the group consisting of chlorobenzene, dichlorobenzenes, trichlorobenzenes, α,α,α-trichlorotoluene, fluorobenzene, difluorobenzenes, trifluorobenzenes, and α,α,α-trifluorortoluene. Preferred organic solvents may be selected from the group consisting of chlorobenzene, dichlorobenzenes, fluorobenzene, and difluorobenzenes. More preferred organic solvents are chlorobenzene and dichlorobenzenes. The most preferred organic solvent is chlorobenzene.

The phase transfer catalysts which may be employed in the present invention may be any phase transfer catalyst which is capable of dissolving the water-soluble nucleophile and the 5- or 6-halomethyl quinoxaline in the organic phase thereby permitting the selective displacement of the halogen group attached to the benzylic position of the heterocyclic compound. The phase transfer catalyst is typically an organic salt (for example, tetraalkyl-ammonium salts, benzyltrimethylammonium salts, etc) that is soluble in both the aqueous phase and the organic phase. Non-limiting illustrative phase transfer catalysts may be selected from the group consisting of tetra-n-butyl-ammonium chloride, benzyltrimethylammonium chloride, benzyltrimethylammonium hydroxide, tetralkyl ammonium salts, tetraalkyl sulfonium salts, and cetyltrimethylammonium salts.

The 5- and 6-halomethyl quinoxalines and the nucleophiles may be reacted in relative amounts ranging from about 1:1 to about 1:100, and preferably from about 1:10 to about 1:30, respectively. The 5- and 6-halomethyl quinoxalines and the nucleophiles may be reacted at temperatures ranging from about 25° C. to about 150° C., preferably from about 25° C. to about 100° C., and at pressures ranging from ambient to about 100 psig, and preferably ambient.

The present invention is further illustrated by the following examples which are presented for purposes of demonstrating, but not limiting, the preparation of the compounds and compositions of this invention.

EXAMPLES

Synthesis of Methyl-quinoxaline from OTD (Ortho-toluenediamine)

To a solution of 122 g of ortho-toluenediamine (1.0 mole) dissolved in 500 cc of 2 M acetic acid, 250 cc of 4 M sodium acetate solution was added with stirring. The mixture was heated up to 60° C. and poured rapidly into a solution of 298.4 g (1.05 moles) of sodium glyoxal bisulfite in 1500 cc of water previously heated to 60° C. The resulting dark solution was stirred for one hour and it was then cooled down in an ice bath until the temperature had dropped below 10° C. The solution was then neutralized with 120 g of sodium hydroxide pellets. After the sodium hydroxide had dissolved, 500 g of potassium carbonate was added. During the addition of alkali, the solution turned red and a black oil separated out. Most of the oily amine was removed by extraction with pentane or hexane and the combined organic phase was dried over $MgSO_4$, filtered and vacuum dried to give a brown oil that upon distillation gave methyl-quinoxaline (92 g) as a clear pale yellow to colorless liquid (80% yield).

Example 2

Preparation of a Chlorobenzene Solution of 6-bromomethyl-quinoxaline

In a 50 ml flask, 6-methyl-quinoxaline (1.25 g, 8.68 mmol) was dissolved together with N-bromosuccinimide (2.32 g, 13.0 mmol) and benzoyl-peroxide (0.15 g, 0.62 mmol) in 31 g of chlorobenzene. The solution was stirred with heating at 85° C. for 2.0 hours to yield a reddish solution. The molar concentrations are shown in the following table:

| Solvent | [6QX] | [NBS] | [BP] |
| --- | --- | --- | --- |
| ClPh | 0.31 | 0.46 | $2.2 \times 10^{-2}$ |

Analysis of the reddish solution by GC-MS showed mostly the formation of compounds 1 while compound 2 (ring bromination) was not detected:

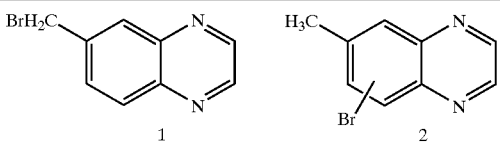

| | Reaction Time = 120 min | |
|---|---|---|
| Product | % Selectivity | % Conversion |
| 1 | 97.0 | 95.0 |
| Unknowns | 3.0 | 2.5 |

The light reddish solution of 6-bromomethyl-quinoxaline was used to prepare 6-hydroxymethyl-quinoxaline as shown in the examples below.

Example 3

Preparation of a Solid Sample of 6-bromomethyl-quinoxaline

In a 100 ml flask, 6-methyl-quinoxaline (2.5 g, 17.4 mmol) was dissolved together with N-bromosuccinimide (4.63 g, 19 mmol) and benzoyl peroxide (0.3 g, 1.24 mmol) in 70 g of 1,2-dichloroethane. The solution was refluxed for 150 minutes and analyzed. The concentrations of the reactants and some of their molar ratios are shown below:

| Solvent | [6QX] | [NBS] | [BP] | [NBS]/[6QX] | [6QX]/[BP] |
|---|---|---|---|---|---|
| 1,2-DCE | 0.31 | 0.46 | 0.022 | 1.5 | 14 |

| | Total Reaction Time = 150 min | |
|---|---|---|
| Product | % Selectivity | % Conversion |
| 1 | 93.4 | 85.0 |
| 2 | 1.6 | 1.5 |
| 3 | 5.0 | 4.6 |

The solution was cooled in the freezer overnight and the solid residue was separated by filtration. The solid was washed with pentane and the washings were combined with the liquid fraction. The clear reddish solution was then vacuum dried to give an orange solid that was used in the preparation of 6-hydroxymethyl-quinoxaline.

Example 4

Reflux of a Chlorobenzene Solution of 6-bromomethyl-quinoxaline with an Aqueous Solution of Sodium Hydroxide A sample of solution of 6-bromomethyl-quinoxaline in chlorobenzene prepared in Example 2 (3.90 g of solution) was mixed with 4 ml of 1.9 M aqueous sodium hydroxide and the two-phase liquid was refluxed for 30 minutes. The chlorobenzene phase was analyzed by gas chromatography and mass spectroscopy. Most of the 6-bromomethyl-quinoxaline remained unreacted. Careful GC-MS analysis of the organic phase showed the presence of traces of 6-hydroxymethyl-quinoxaline. Although the presence of a base was expected to react with the bromo-compound to yield 6-hydroxymethyl-quinoxaline, reflux of the two phase mixture (water/chlorobenzene) was inappropriate for the reagents to get mixed yielding only a trace of the desired product.

Example 4 shows that mixing a chlorobenzene solution of 6-bromomethyl-quinoxaline with an aqueous alkali hydroxide solution is not an efficient method because of the unfavorable partition coefficient of the base in the organic phase.

Example 5

Reflux of a Chlorobenzene Solution of 6-bromomethyl-quinoxaline with an Aqueous Solution of Sodium Hydroxide in the Presence of a Phase-transfer Catalyst In a 50 ml flask, the solution of 6-bromomethyl-quinoxaline in chlorobenzene prepared in Example 2 (24.1 g of solution) was mixed with an aqueous solution of sodium hydroxide prepared by dissolving 1.7 g of sodium hydroxide in 4 ml of water. A phase-transfer catalyst (tetra-n-butyl-ammonium chloride) was added to the two-phase liquid mixture (0.1 g) followed by a gentle reflux. Upon heating, the reddish chlorobenzene solution turned dark-brown. The reaction was stopped after 30 minutes refluxed and the aqueous phase was neutralized with a 4 M solution of sulfuric acid. The chlorobenzene phase (reddish color) was separated and dried over anhydrous $MgSO_4$.

GC-MS analysis of the chlorobenzene phase showed absence of 6-bromomethyl-quinoxaline and the presence of 6-hydroxymethyl-quinoxaline. The chlorobenzene solution was evaporated under vacuum and the solid residue was washed with pentane to remove some remaining organic impurities. The brown solid residue (~0.5 g, 52% yield)) was analyzed by GCMS showing mostly 6-hydroxymethyl-quinoxaline (80% purity).

Example 5 shows that in the presence of a phase transfer catalyst, the reaction can proceed with acceptable rates.

Example 6

Reflux of a Suspension of 6-bromomethyl-quinoxaline in Aqueous Sodium Hydroxide

The orange solid obtained in Example 3 was mixed with 50 ml of potassium hydroxide (1.42 M). The reaction mixture was heated to reflux with the aid of a heating mantle for 20 minutes and analyzed. The aqueous suspension was extracted with 250 ml of methylene chloride (5 times, 50 ml each) and the extracts were dried over anhydrous $MgSO_4$, filtered and vacuum dried to give 1.5 g of a brownish solid (65% yield) composed of 80% 6-hydroxymethyl-quinoxaline.

Upon heating, the 6-bromomethyl-quinoxaline melts and strong stirring is required to get the organic phase in contact with the alkali. When heating, the organic phase slowly turned brown particularly in the areas where the flask was in contact with the heating mantle. Example 6 shows that some of the compound decomposed during heating and consequently a milder heating source may be used.

Example 7

Direct Reaction Between Solid 6-bromomethyl-quinoxaline and Aqueous Base

A sample of 6-bromomethyl-quinoxaline (1.0 g) was placed in a 50 ml flask and 14.0 g of a solution of KOH (prepared by dissolving 4 g of KOH pellets in 20 g of water) was added. The yellowish suspension was heated in a water bath to 80° C. and maintained at that temperature for about 30 minutes. The aqueous solution was then neutralized with dilute aqueous sulfuric acid and the organic product was extracted with 150 ml of chloroform. The extracts were dried over anhydrous magnesium sulfate, filtered and vacuum dried to give a dark yellow solid (1.0 g) that was washed with pentane and ether to give 0.6 g (~80% yield) of a yellow solid mostly composed of 6-hydroxymethyl-quinoxaline.

Example 7 shows that when a water bath at 80° C. is used as a heating source, the organic phase does not turned completely brown but dark yellow. The addition of a phase transfer catalyst minimized even more the formation of brown products (tars) resulting from the thermal decomposition of 6-bromomethyl-quinoxaline. Thus, minimizing heating and finding a solvent media that favors the solution of both 6-bromomethyl-quinoxaline and the base seems to be the most appropriate procedure to make 6-hydroxymethyl-quinoxaline from its bromo compound.

Example 8

Synthesis of 6-hydroxymethyl-quinoxaline from 6-bromomethyl-quinoxaline and Benzyltrimethyl-ammonium Hydroxide In a 50 ml flask, 6-methyl-quinoxaline (1.25 g, 8.68 mmol) was dissolved together with N-bromosuccinimide (2.32 g, 13.0 mmol) and benzoyl peroxide (0.15 g, 0.62 mmol) in 31 g of chlorobenzene. The solution was stirred with heating at 85° C. for 2.0 hours to yield a reddish solution. The solution was cooled down to room temperature and one volume of pentane was added to facilitate the precipitation of succinimides. The solid was filtered (1.6 g), washed with pentane and the extracts were combined with the chlorobenzene solution. This solution was then vacuum dried to give a yellow solid mainly composed of 6-bromomethyl-quinoxaline (1.92 g). This solid was dissolved in 38 g of THF and mixed with 4.24 g of a 40% commercial aqueous solution of benzyltrimethyl ammonium hydroxide. Samples were analyzed during the course of the reaction showing a progressive conversion of 6-bromomethyl-quinoxaline into the hydroxy derivative. The pale yellow solution was stirred at room temperature overnight until the reaction was completed and no other by-products were detected by GCMS analysis. The alkaline solution was neutralized with dilute sulfuric acid (1 M) and pH adjusted with sodium bicarbonate. The solution was vacuum dried to give a yellow residue (2.5 g) that was dissolved in methylene chloride and extracted with water to remove the organic salt. The methylene chloride solutions were dried over anhydrous $MgSO_4$ and the solution evaporated to give a pale yellow solid mostly composed of 6-hydroxymethyl-quinoxaline (1.15 g, ~83% yield).

Example 8 shows that the use of a phase transfer reagent minimizes decomposition of 6-bromomethyl-quinoxaline (no tars) because heating is not required to improve the miscibility of the phases.

Example 9

Analytical Data of 6-hydroxymethyl-quinoxaline

A sample of the brownish solid obtained in Example 6 was further purified by distillation. The product was isolated as a white solid that showed the following analytical data: MS (70 ev): 160 ($M^+$); 143 ($M^+$—OH); 131 ($M^+$—OH—C); $^1H$ NMR ($CDCl_3$): 4.85 (s, 2H, =$CH_2$), 5.2 (br, 1H, —OH), 7.65 (d, 1H, C—H aromatic), 7.90 (d, 1H, C—H aromatic), 7.95 (s, 1H, C—H aromatic), 8.65 (s, 2H, C—H aromatic).

Example 10

Synthesis of 6-n-butylaminomethyl-quinoxaline

In a 50 ml flask, 6-methyl-quinoxaline (1.25 g, 8.68 mmol) was dissolved together with N-bromosuccinimide (2.32 g, 13.0 mmol) and benzoyl-peroxide (0.15 g, 0.62 mmol) in 31 g of chlorobenzene. The solution was stirred with heating at 85° C for 2.0 hours to yield a reddish solution. The solution was cooled down to room temperature and one volume of pentane was added to facilitate the removal of succinimides. The precipitate was washed with pentane and the extracts were combined with the chlorobenzene solution. The yellow solution was vacuum dried to give a yellow residue mainly composed of 6-bromomethyl-quinoxaline. The yellow solid was dissolved in 19.0 g of n-butylamine to give a yellow solution that was stirred at room temperature for ~5 minutes. Analysis of a sample showed that the 6-bromomethyl-quinoxaline was consumed to give exclusively 6-n-butylaminomethyl-quinoxaline as a deep yellow oil (1.71 g, 92% over all yield). MS (70 ev): 215 $M^+$, 172 ($M^+$—$CH_3$—$CH_2$—$CH_2$), 143 ($M^+$—$CH_3$—$CH_2$—$CH_2$—$CH_2$).

Example 10 shows that some organic solvent-soluble nucleophiles (alkylamines, for example) can readily react with 6-bromomethyl-quinoxaline because the compound is completely soluble in the organic phase. Example 10 shows that 6-bromomethyl-quinoxaline completely reacted with n-butylamine in few minutes at room temperature to give 6-n-butylaminomethyl-quinoxaline. In this example, n-butylamine acted as both the nucleophile and the solvent.

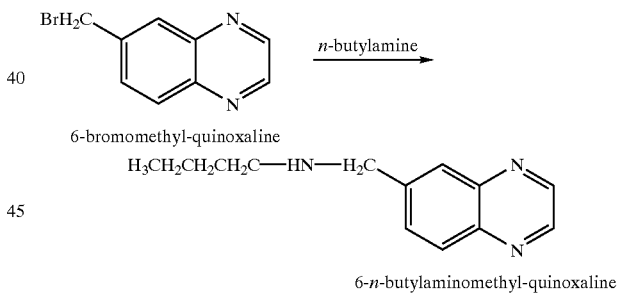

Throughout this application, various publications have been referenced. The disclosures in these publications are incorporated herein by reference in order to more fully describe the state of the art.

1. a) G. W. H. Cheeseman in "*Advances in Heterocyclic Chemistry*" by A. R. Katritzky Academic Press. Vol. 2. pp. 203–221. 1963. b) G. W. H. Cheeseman and E. S. G. Werstiuk 367–419 in "*Advances in Heterocyclic Chemistry*" by A. R. Katritzky Academic Press. Vol. 22. pp. 203–221. 1978 c) J. C. Cavagnol, F. Y. Wiselogle, *J. Am. Chem. Soc.,* 69, 795, 1947.
2. O. Gawron, P. E. Spoerri, *J. Am.Chem. Soc.,* 67, 514, 1945.
3. R. Mizzoni, P. E. Spoerri, *J. Am.Chem. Soc.,* 67, 1652, 1945.
4. O. Gawron, A. Rampal, P. Johnson, *J. Am.Chem. Soc.,* 94, 5396, 1972.

5. R. C. DeSelms, R. J. Greaves, W. R. Schleigh, *J. Heterocyclic Chem.*, 11, 595, 1974.
6. Venet et al. U.S. Patent No. 5,028,606 (1991).
7. (a) R. Granger, S. Deadwyler, M. Davis, B. Moskovitz, M. Kessler, G. Rogers, G. Lynch, Synapse, 22, pp. 332–337, 1996. (b) G. Lynch, M. Kessler, G. Rogers, J. Ambross-Ingerson, R. Granger, R. S. Schehr, *International Clinical Psycopharmacology*, 11, pp.13–19, 1996.
8. 2,3-Pyrazinedicarboxylic acid: "*Organic Synthesis*" Coll. Vol. 4 pp. 824–827, J. Wiley & Sons, Inc. NY., 1963.
9. D. F. Gavin, U.S. Pat. No. 3,960,963 (1976).

While a number of embodiments of this invention have been represented, it is apparent that the basic construction can be altered to provide other embodiments which utilize the invention without departing from the spirit and scope of the invention. All such modifications and variations are intended to be included within the scope of the invention as defined in the appended claims rather than the specific embodiments which have been presented by way of example.

What is claimed is:

1. A method for preparing a 5- or 6-benzyl functionalized compound having Formula (I)

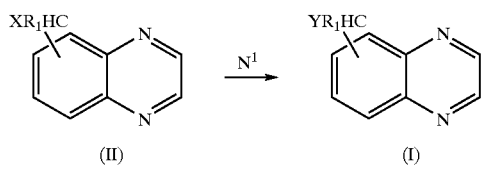

which comprises contacting a compound having Formula (II) in an organic solvent with an aqueous solution of a water-soluble nucleophile, $N^1$, containing moiety Y, in the presence of a phase transfer catalyst; wherein X is chloro or bromo; $R_1$ is selected from the group consisting of hydrogen and branched and unbranched alkyl and aryl groups having from 1 to 9 carbon atoms; and Y is hydroxy.

2. The method according to claim 1, wherein the compound having Formula (I)

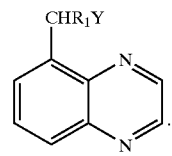

3. The method according to claim 1, wherein the compound having Formula (I) is:

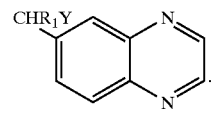

4. The method according to claim 1, wherein X is chloro.
5. The method according to claim 1, wherein X is bromo.
6. The method according to claim 1, wherein $R_1$ is selected from the group consisting of hydrogen and branched and unbranched alkyl and aryl groups having from 1 to 6 carbon atoms.
7. The method according to claim 1, wherein the water-soluble nucleophile, $N^1$, is selected from the group consisting of alkali hydroxides and alkaline earth hydroxides.
8. The method according to claim 1, wherein the water-soluble nucleophile, $N^1$, is selected from the group consisting of lithium hydroxide, sodium hydroxide, and potassium hydroxide.
9. The method according to claim 1, wherein the organic solvent is selected from the group consisting of chlorobenzene, dichlorobenzenes, trichlorobenzenes, $\alpha,\alpha,\alpha$-trichlorotoluene, fluorobenzene, difluorobenzenes, trifluorobenzenes, and $\alpha,\alpha,\alpha$-trifluorortoluene.
10. The method according to claim 1, wherein the phase transfer catalyst is selected from the group consisting of tetra-n-butyl-ammonium chloride, benzyltrimethylammonium chloride, benzyltrimethylammonium hydroxide, tetralkyl ammonium salts, tetraalkyl sulfonium salts, and cetyltrimethylammonium salts.

* * * * *